US011986403B2

(12) United States Patent
Ballas et al.

(10) Patent No.: US 11,986,403 B2
(45) Date of Patent: May 21, 2024

(54) MODULAR ADJUSTABLE PROSTHETIC VOLUME COMPENSATION SYSTEM

(71) Applicants: Gary Joseph Ballas, Redmond, WA (US); Michael Thomas Ballas, Snohomish, WA (US)

(72) Inventors: Gary Joseph Ballas, Redmond, WA (US); Michael Thomas Ballas, Snohomish, WA (US)

( * ) Notice: Subject to any disclaimer, the term of this patent is extended or adjusted under 35 U.S.C. 154(b) by 200 days.

(21) Appl. No.: 17/422,158

(22) PCT Filed: Jan. 23, 2020

(86) PCT No.: PCT/US2020/014759
§ 371 (c)(1),
(2) Date: Jul. 9, 2021

(87) PCT Pub. No.: WO2020/154485
PCT Pub. Date: Jul. 30, 2020

(65) Prior Publication Data
US 2022/0110768 A1    Apr. 14, 2022

Related U.S. Application Data

(60) Provisional application No. 62/796,731, filed on Jan. 25, 2019.

(51) Int. Cl.
*A61F 2/74* (2006.01)
*A61F 2/78* (2006.01)
(Continued)

(52) U.S. Cl.
CPC ............ *A61F 2/7843* (2013.01); *A61F 2/748* (2021.08); *A61F 2/80* (2013.01); *A61F 2002/5083* (2013.01)

(58) Field of Classification Search
CPC .......... A61F 2/60; A61F 2/602; A61F 2/7843; A61F 2/748; A61F 2/80; A61F 2002/501;
(Continued)

(56) References Cited

U.S. PATENT DOCUMENTS 2,196,145 A * 4/1940 Stanziale ................. A41H 9/02
33/10
3,671,980 A    6/1972 Baird
(Continued)

FOREIGN PATENT DOCUMENTS

EP    0 019 612 A1    11/1980

OTHER PUBLICATIONS

International Search Report and Written Opinion, mailed Apr. 21, 2020, issued in corresponding International Application No. PCT/US2020/014759, filed Jan. 23, 2020, 12 pages.

*Primary Examiner* — Christie Bahena
(74) *Attorney, Agent, or Firm* — CHRISTENSEN O'CONNOR JOHNSON KINDNESS PLLC (57) ABSTRACT

Systems and methods for modular adjustable prosthetic volume compensation are disclosed herein. In one embodiment, a system for adjusting fit of a prosthetic device includes: a pump having a bleed actuator, a plunger and a pressure bulb. The system also includes a bladder fluidically coupled to the pump. The bladder lines a posterior section of an interior of a prosthetic device. A volume of the bladder is changeable by a pumping action of the pump. The volume of the bladder at least partially determines a space available inside the prosthetic device. The bleed actuator is configured to decrease a volume of the bladder. The plunger in operation squeezes the pressure bulb of the pump.

13 Claims, 12 Drawing Sheets

(51) Int. Cl.
*A61F 2/80* (2006.01)
*A61F 2/50* (2006.01)

(58) Field of Classification Search
CPC ...... A61F 2002/5012; A61F 2002/5083; A61F 2002/785
See application file for complete search history.

(56) References Cited

U.S. PATENT DOCUMENTS

| | | | |
|---|---|---|---|
| 5,108,456 A * | 4/1992 | Coonan, III | A61F 2/7843 623/36 |
| 5,133,776 A * | 7/1992 | Crowder | A61F 2/7843 128/DIG. 20 |
| 5,697,974 A | 12/1997 | Wang | |
| 6,416,703 B1 | 7/2002 | Kristinsson et al. | |
| 6,585,774 B2 | 7/2003 | Dean, Jr. et al. | |
| 7,655,049 B2 * | 2/2010 | Phillips | A61F 2/80 623/37 |
| 8,758,449 B2 | 6/2014 | Caspers | |
| 9,345,590 B2 | 5/2016 | Arabian et al. | |
| 2011/0247321 A1 * | 10/2011 | Streeter | A61F 2/7843 60/329 |
| 2017/0266021 A1 | 9/2017 | Bernhardt et al. | |

\* cited by examiner

MODULAR ADJUSTABLE PROSTHETIC VOLUME COMPENSATION SYSTEM

CROSS-REFERENCES TO RELATED APPLICATIONS

The present application is a National Stage of International Application No. PCT/US2020/014759, filed Jan. 23, 2020, which claims the benefit of a U.S. Provisional Application No. 62/796,731 filed on Jan. 25, 2019.

TECHNICAL FIELD

The present invention relates generally to prosthetics and more specifically to managing the fit of a prosthetic device to a residual limb.

BACKGROUND

Many amputees are dissatisfied with the comfort and fit of their prosthetic device. Amputees typically have daily fluctuations in limb volume that result in improper fit of the sockets of their prosthetic devices, causing discomfort, skin breakdown and instability during ambulation. The fit of the socket portion, which is the portion of the prosthetic device that fits around the amputated or "residual" limb, is very sensitive to changes in volume of the residual limb. When limb volume reduces, as commonly occurs throughout the day, the residual limb often moves or "pistons" up and down in the socket, or translates in lateral or rotational degrees of freedom in the socket, altering the fit of the socket and potentially inducing sores on the skin of the residual limb. Skin and underlying soft tissue injury is debilitating for the amputee and can lead to secondary disability and a worsened quality of life. Additionally, many amputees have neuropathy, which results in a loss of sensation in the residual limb and making it difficult to manage pressure in the socket.

The present standard of care and common practice for an amputee to address limb volume changes is to doff the prosthetic, usually multiple times per day, by either adding or removing additional sock plies. The amputee places socks over the residual limb and then places the residual limb in the socket. These socks come in various thicknesses called "plies," with an individual typically having multiple sock plies such as one-ply socks, three-ply socks, and five-ply socks. These multiple plies require the amputee to doff the prosthetic multiple times throughout the day to allow removing or adding the plies to adjust the fit of the residual limb in the socket. The socket is then donned again until another change is required. This process allows only discrete step changes in the fit and is often inconvenient to do during daily life given the need for alternate means of stability with the prosthetic removed. Furthermore, amputees may choose to only doff/don their prosthetic in private. These inconveniences hinder the amputee from maintaining an optimum secure fit for ambulation, and equally important, the ability to minimize the pressure at all times when they are not intending to move or stand on their prosthetic, such as while working at a desk, watching TV, etc. This latter aspect is important since limb volume reduction is a function of applied pressure and time under pressure. The use of sock plies for fit adjustments makes it impractical to maximize the time at the lowest possible pressure, therefore hindering limb volume recovery that occurs when the limb is exposed to lowest possible pressure. Finally, there is a hassle of carrying and the recurring cost associated with use of multiple layers of specialized sock plies that could be reduced or eliminated by an alternate technology.

Accordingly, improved systems and methods are needed for improving the fit between the residual limb and prosthetic device.

SUMMARY

This summary is provided to introduce a selection of concepts in a simplified form that are further described below in the Detailed Description. This summary is not intended to identify key features of the claimed subject matter.

Briefly, the inventive technology is directed to improving the fit between amputee's residual limb and a prosthetic device by compensating for volume changes of the limb. In some embodiments, an inflatable bladder is inserted into the prosthetic device (also referred to as "prosthetic" for simplicity and brevity). Inflating and deflating the bladder changes the volume of the bladder, therefore adjusting the pressure between the residual limb and the prosthetic device. As a result, the pressure change caused by limb volume change of the partial limb inside the prosthetic device may be compensated in order to maintain required support for the limb.

In operation, an amputee may pressurize the bladder through a pump actuator (e.g., a lever for manual actuation or a motor for motorized actuation). In some embodiments, the pump is attached to an outside posterior portion of the prosthetic device, thus providing an easy and discreet access to the pump actuator. In some embodiments, the pump actuator moves along an up-down path, where the "up" stroke is a pumping stroke. As a result, the fabric that covers the pump is crumpled or folded during the pumping stroke, therefore avoiding stretching the fabric that would otherwise increase pumping effort and discomfort of the user.

In some embodiments, fluid (e.g., air) is pumped by displacing certain volume of fluid from a flexible pressure bulb into the bladder. In operation, the amount of such volume displacement may be utilized to control pressure inside the flexible pressure bulb and, consequently, inside the bladder. In some embodiments, the volume displacement may be controlled by an adjustable position of the pump actuator.

In some embodiments, the amputee may depressurize the bladder by a bleed actuator positioned away from a top surface of the pump. For example, the bleed actuator may be positioned on a side surface of the pump to avoid its accidental activation during the pumping strokes.

In some embodiments, the bladder is positioned along a posterior part of the prosthetic, thus biasing amputee's shin (also referred to as tibial plateau) toward an anterior part of the prosthetics. The anterior part of the prosthetics may be shaped to correspond to a generally wedge-like shape of the shin, therefore preventing or at least reducing rotation of the residual limb inside the prosthetic device.

While the inventive technology is described in the context of a typical below knee (BK) transtibial amputee, it should be understood that the inventive systems and methods are applicable to above knee (AK) transfemoral amputees and even amputations associated with arms. Furthermore, some embodiments of the inventive technology may benefit non-amputee users that need to apply and release pressure to any part of the body. Some non-limiting examples of such use are treatment or prevention of lymphedema, bed sores, deep vein thrombosis, chronic venous insufficiency and/or other venous conditions.

Additionally, the inventive technology may also benefit users in the non-medical applications, such as in sporting equipment for adjustment of pressure applied to sensitive areas. Some non-limiting examples of such use are ski boots, cycling shoes, and bicycle seats.

In one embodiment, a system for adjusting fit of a prosthetic device includes: a pump having a bleed actuator, a plunger and a pressure bulb. A bladder is fluidically coupled to the pump, where the bladder lines a posterior section of an interior of the prosthetic device. A volume of the bladder is changeable by a pumping action of the pump, and the volume of the bladder at least partially determines a space available inside the prosthetic device. The bleed actuator is configured to decrease a volume of the bladder. The plunger in operation squeezes the pressure bulb of the pump.

In one aspect, the system also includes the prosthetic device configured to receive a partial limb.

In one aspect, a neck of the bladder protrudes through a slot on the prosthetic device.

In another aspect, the pump is mounted to an outer posterior of the prosthetic device.

In one aspect, the pump includes a pump actuator configured to move along an up-down path.

In one aspect, fluid is pumped into the bladder during upward strokes of the pump actuator.

In another aspect, the bleed actuator is situated away from a top surface of the pump and away from the up-down path of the pump actuator such that the bleed actuator can be operated through clothing.

In one aspect, a barb of the pump is directly connected to a bladder port of the bladder.

In another aspect, the displacement of the plunger into the pressure bulb is adjustable, where the displacement of the plunger at least in part determines a maximum pressure inside the bladder.

In one aspect, the plunger includes a rotating wheel that rotates when in contact with the pressure bulb.

In another aspect, the pressure bulb and the bladder are fluidically connected through a one-way valve and a high-pressure.

In one aspect the system also includes: at least one sensor configured to measure the pressure inside the bladder; a controller configured to receive a sensor signal; a first actuator configured to drive the plunger; and a second actuator configured to open and close the bleed actuator in response to a controller signal.

In one aspect, the pump is an air pump.

In another aspect, the pump is liquid pump, where the bladder is fluidically coupled to the pump with a high-pressure tubing, and where the bladder is fluidically coupled to an external liquid reservoir with a low-pressure tubing.

In one embodiment, a system for adjusting fit of a prosthetic device includes: a pump having a barb that is oriented toward a posterior of the prosthetic device; and a bladder having a bladder port that is directly connected to the barb of the pump. The bladder lines the posterior section of an interior of a prosthetic device. A volume of the bladder is changeable by a pumping action of the pump, and the volume of the bladder at least partially determines a space available inside the prosthetic device. The bleed actuator is configured to decrease a volume of the bladder.

In one embodiment, a method for adjusting fit of a prosthetic device includes: lining a bladder along an inside posterior portion of the prosthetic device; increasing a volume of the bladder by pumping a fluid into the bladder by squeezing a pressure bulb of the pump by a plunger of the pump actuator; and decreasing the volume of the bladder by releasing the fluid from the bladder through a bleed valve.

In one aspect, pumping the fluid into the bladder includes moving the pump actuator in an up-down path, and the fluid is pumped into the bladder during upward strokes of the pump actuator.

In another aspect, the bleed actuator is situated away from a top surface of the pump and away from the up-down path of the pump actuator.

In one aspect, a bladder port of the bladder and a barb of the pump are directly connected without an intervening hose.

In another aspect, the method also includes: adjusting a travel of the plunger into the pressure bulb, where the travel of the plunger into the pressure bulb at least in part determines a maximum pressure inside the bladder.

In one aspect, pumping the fluid into the bladder is done manually with one hand through clothing.

In another aspect, releasing the fluid from the bladder is done manually with one hand through clothing.

BRIEF DESCRIPTION OF THE DRAWINGS

The foregoing aspects and many of the attendant advantages of the inventive technology will become more readily appreciated as the same are understood with reference to the following detailed description, when taken in conjunction with the accompanying drawings, wherein.

DETAILED DESCRIPTION

While several embodiments have been illustrated and described, it will be appreciated that various changes can be made therein without departing from the spirit and scope of the claimed subject matter.

Figure 1:
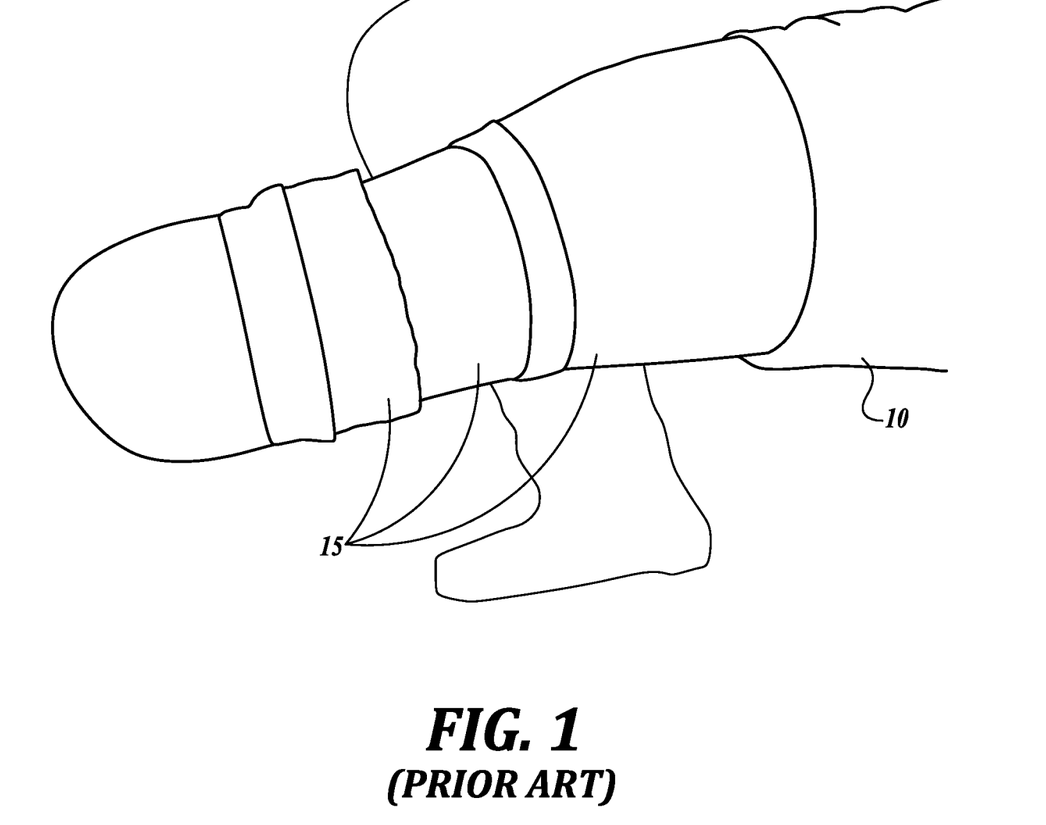
FIG. 1 is perspective view of a prosthetic volume compensation system in accordance with conventional technology.

FIG. 1 is perspective view of a prosthetic volume compensation system in accordance with conventional technology. FIG. 1 shows sock plies 15 worn over a partial limb 10. An amputee adds and removes sock plies to increase limb comfort and/or stability depending on the body position, limb volume change, limb exertion, etc. However, in many applications such adding and removing of the sock plies is inconvenient and cannot be done discreetly. Additionally, adding and removing the sock plies does not allow for a continuous change in material thickness, instead the thickness changes are discrete increments/decrements corresponding to the thickness of particular sock plie.

Figure 2:
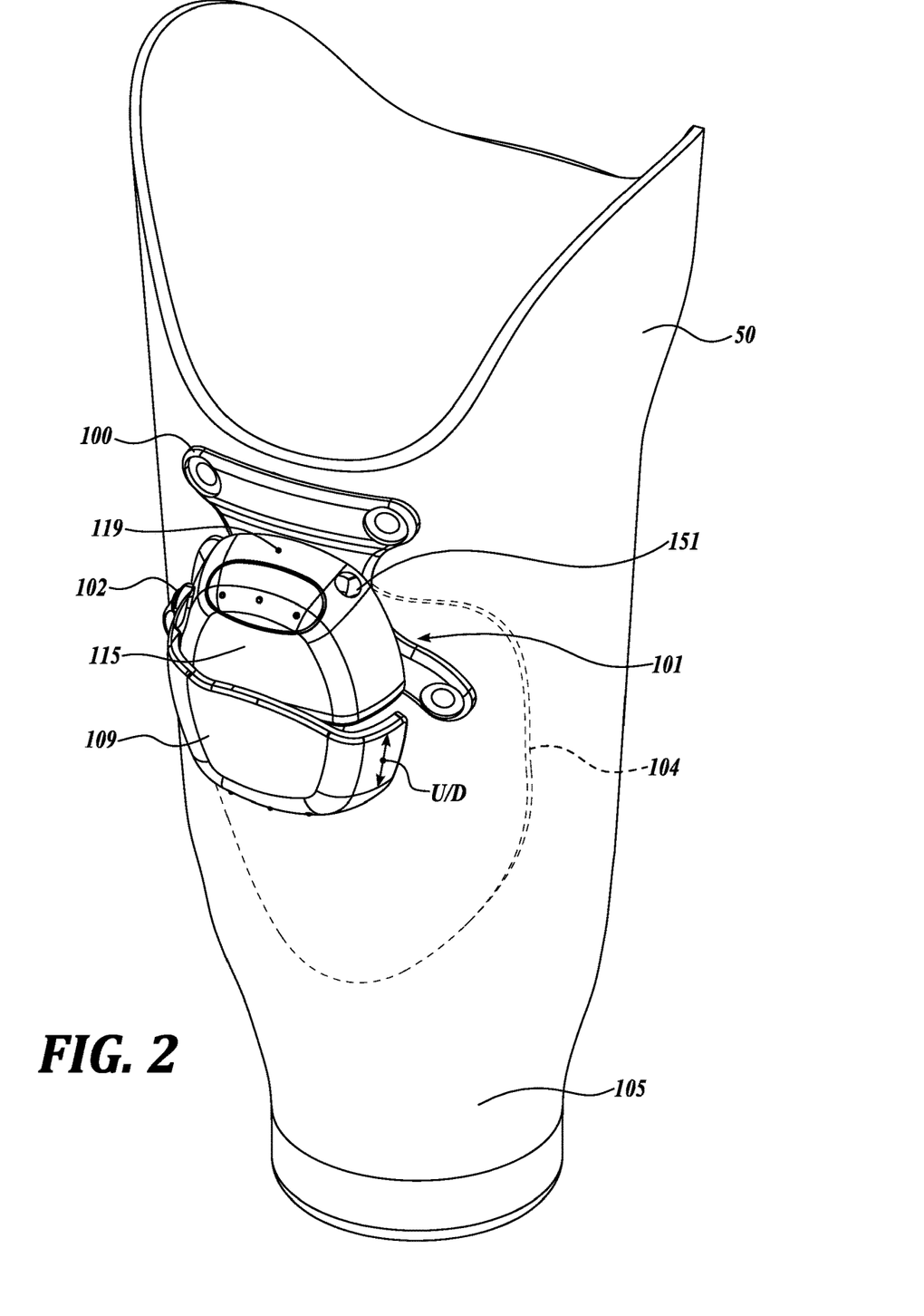
FIG. 2 is a perspective view of a prosthetic volume compensation system when attached to a prosthetic device in accordance with an embodiment of the present technology.

FIG. 2 is a perspective view of a prosthetic volume compensation system when attached to a prosthetic device in accordance with an embodiment of the present technology. A pump assembly 101 may be attached to the posterior portion of a prosthetic socket 105 of a prosthetic device 50. In operation, the prosthetic socket 105 houses the residual limb of an amputee. In some embodiments, the socket 105 may securely couple the residual limb to a prosthetic foot (not shown) to allow mobility. The pump assembly 101 may be attached to the prosthetic device 50 by a pump mount 100 using, for example, fasteners or epoxies. In some embodiments, the pump mount 100 may include features for attaching the pump assembly to variety of shapes and contours of the prosthetic device 50. In different embodiments, the pump mount 100 may be attached to the prosthetic device 50 as an aftermarket product, or as an integral part of the prosthetic device 50 that is added during the manufacturing of the device.

The pump assembly 101 may include a pump frame 115 to which a pump lever 109 is attached by, for example, a hinge. In operation, the pump lever 109 moves a pump actuator inside the pump (not shown). An amputee may move the pump lever 109 up/down, as indicated by arrows U/D, to pump fluid into a bladder 104. For example, the up motion may correspond to a fluid-pumping stroke, while the down motion corresponds to a lever-return stroke. In some embodiment, such up/down motion of the pump lever 109 avoids stretching and pulling of the fabrics of amputee's clothing. Instead, the clothing that covers the pump is crumpled or folded up during the pumping stroke, and then straightened back down during the return stroke, therefore limiting the intensity of the pumping force and discomfort of the user. In different embodiments, fluid pumped into the bladder fluid may be a gas (e.g., air) or a liquid.

In operation, the pump assembly 101 may provide a continuous range of fit between the residual limb and the interior of prosthetic by inflating/deflating the bladder 104. In some embodiments, the placement and orientation of the pump facilitate pump operation irrespective whether the user sits or stands. A relatively high location of the pump assembly 101 just beneath the proximal posterior lip of the socket allows for a minimum reach, while also being low enough beneath the knee to limit interference with chairs when the amputee is seated. For example, in some embodiments the pump assembly 101 may be placed between amputee's knee and a midpoint of the calf.

The pump assembly 101 may include a bleed actuator 102 that is operationally coupled with the bladder 104 to release the pressure from the bladder. In some embodiments, to avoid an accidental activation of the bleed actuator 102 and the consequent fluid release, the bleed actuator 102 is configured away from the top surface. Thus, a user may press against a top surface 119 for support when moving the pump lever 109 in the fluid-pumping stroke (up), while not accidently activating the bleed actuator that is positioned away from the top surface. In some embodiments, the bleed actuator may be elevated above the surrounding surface (set proud) to ease its tactile identification.

Figure 3:
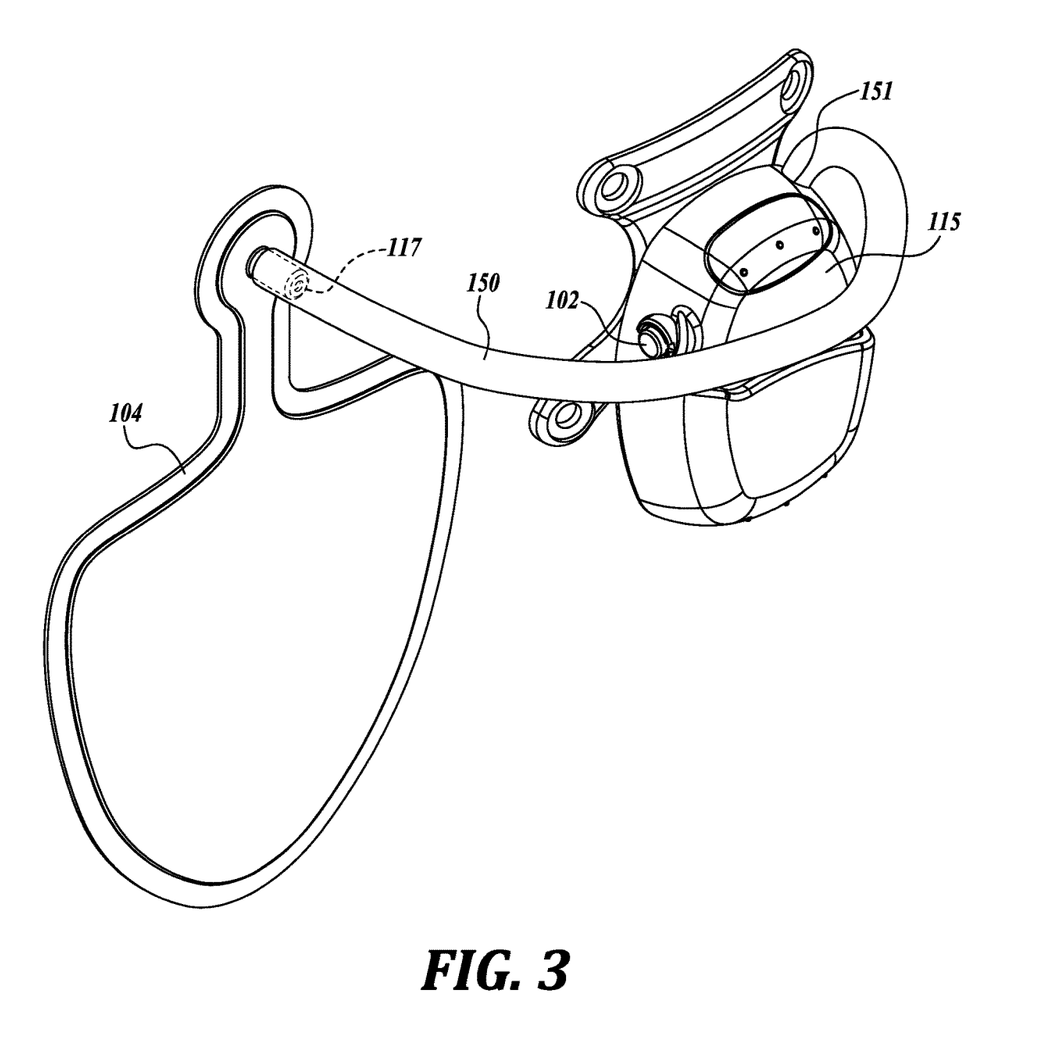
FIG. 3 is a perspective view of a prosthetic volume compensation system in accordance with an embodiment of the present technology.

FIG. 3 is a perspective view of a prosthetic volume compensation system in accordance with an embodiment of the present technology. The illustrated system includes the pump assembly 101, a hose 150 and the bladder 104. The hose 150 provides a path for the fluid from the pump assembly to the bladder (during the fluid-pumping stroke) or from the bladder to the pump assembly (when the bleed actuator is activated). In some embodiments, the bladder 104 and the pump 101 may be connected directly, without an intervening hose 150 that passes through an opening 151 on the pump, as discussed below with reference to FIG. 7.

In different embodiments, the pump may be a piston pump, a pressure bulb pump, or other type of pump. The pump may be operated manually or may be motorized. In some embodiments, the components of the prosthetic volume compensation system may be modular, thus different bladders 104 may be combinable with different pump assemblies 101. In some embodiments, multiple bladders 104 are used to improve the fit and retention of the residual limb. Positioning of the bladder 104 within the prosthetic device is discussed with respect to FIGS. 4 and 5 below.

Figure 4:
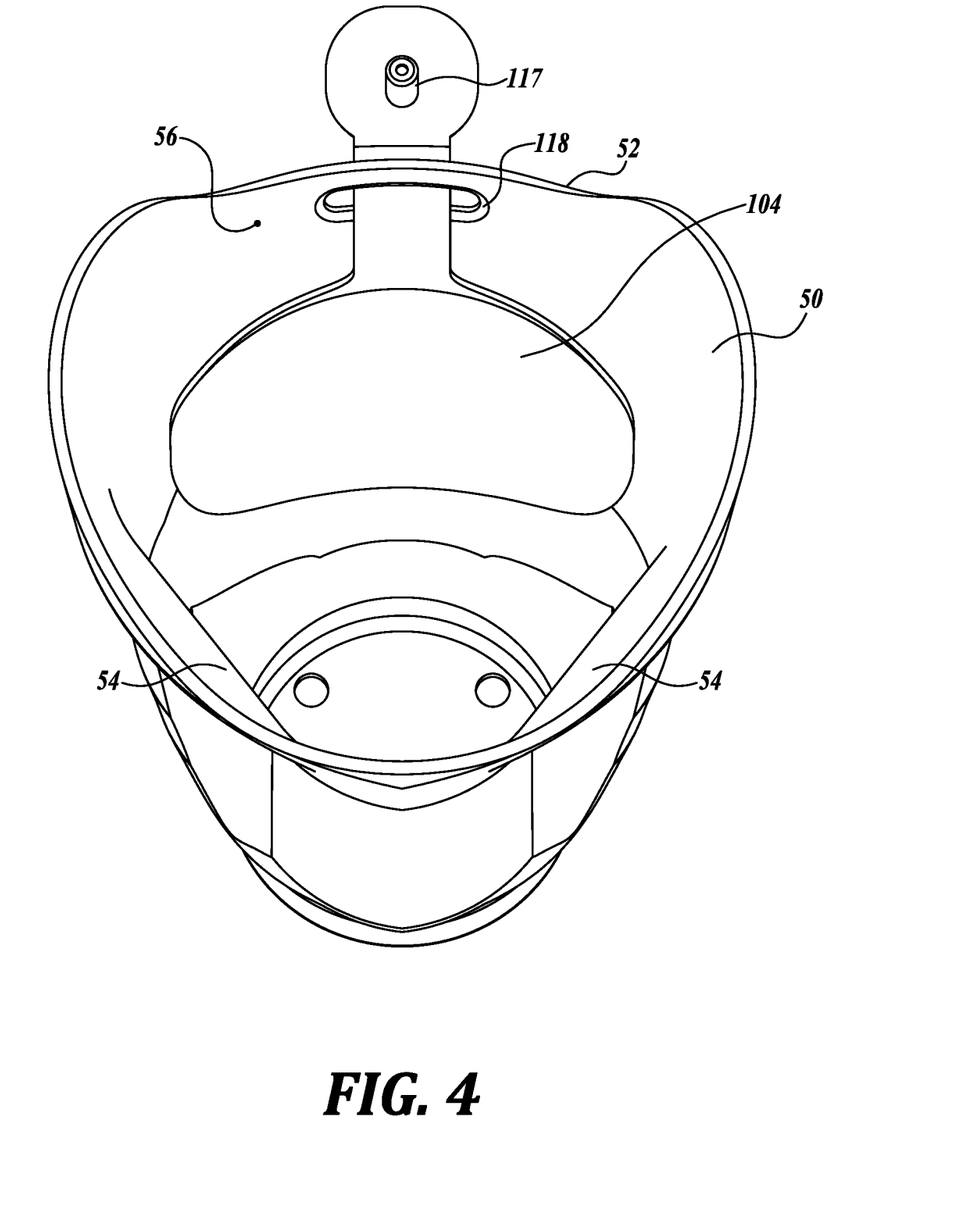
FIGS. 4 and 5 are perspective views of bladder mounting in accordance with an embodiment of the present technology.
Figure 5:
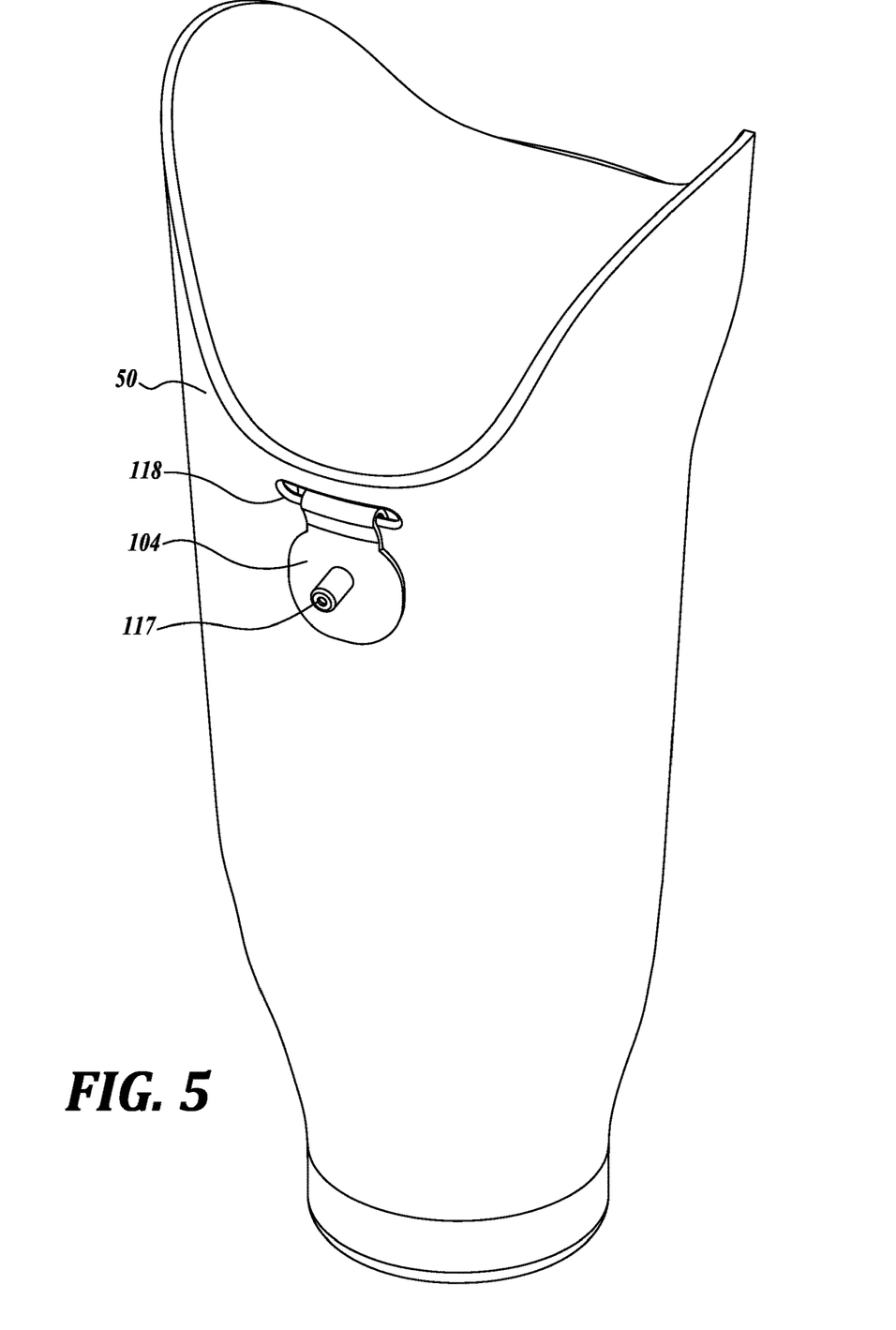

FIGS. 4 and 5 are perspective views of bladder mounting in accordance with an embodiment of the present technology. FIG. 4 illustrates a bladder 104 that lines a posterior section 56 of the prosthetic device 50. Inflating and deflating of the bladder 104 changes the volume available to the amputee's limb, in relation to the swelling of the partial limb. Furthermore, as the bladder 104 is pressurized and inflated, amputee's leg is pushed toward an anterior section 54 of the prosthetic device 50. In some embodiments, the anterior section 54 may be shaped to correspond to a generally wedge-like shape of amputee's shin, therefore preventing or at least reducing a rotation of the residual limb inside the prosthetic device in use.

In different embodiments, a bladder port 117 is passed outside of the prosthetic device 50 through a bladder slot 118 or over a lip 52. The illustrated bladder slot is horizontal, however in other embodiments the bladder slot 118 may be oriented differently. FIG. 5 shows an outside portion of the prosthetic device 50, where the bladder port 117 is exposed for connection with the hose 150 or directly to a corresponding barb on the pump.

Figure 6:
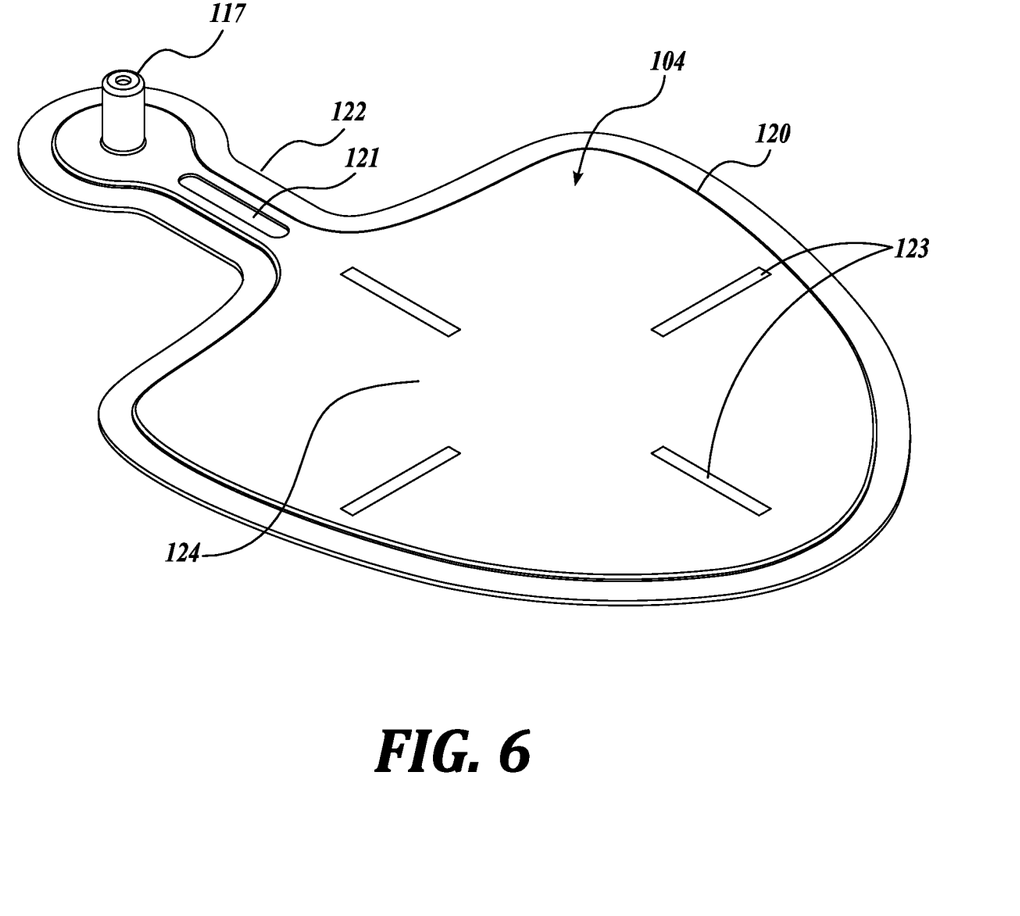
FIG. 6 is a perspective view of a bladder in accordance with an embodiment of the present technology.

FIG. 6 is a perspective view of a bladder in accordance with an embodiment of the present technology. In operation, the bladder 104 relatively easily conforms to the shape of the prosthetic socket 50 and the residual limb, while self-supporting the internal pressures. The bladder 104 may include a seam weld 122 and one or more intermediate welds 123 that limit out-of-plane displacement of the bladder surfaces. In different embodiments, the arrangement of the intermediate welds 123 may limit maximum displacement of the bladder 104. A non-limiting example of such arrangement is a quilted pattern of the intermediate welds 123.

When not inflated, the bladder 104 has a relatively thin cross-section that facilitates insertion of the neck region through the bladder slot 118. In some embodiments, a neck weld 121 limits displacement in the neck region of the bladder 104 to, for example, prevent binding of the neck region inside the bladder slot 118.

In some embodiments, the overall "shield" shape of an active bladder region 124 allows a conformal fit within a typically complex shape of prosthetic's interior that may have a relatively cylindrical portion (in the region of the residual limb calf) that transitions to a generally hemispherical distal portion (in the distal region of the residual limb). Such shape of the bladder may be beneficial when using materials with low elasticity in the in-plane direction. The illustrated shape of the active bladder region 124 may also conform to the interior surface of a typical prosthetics socket with little or no wrinkling.

Figure 7:
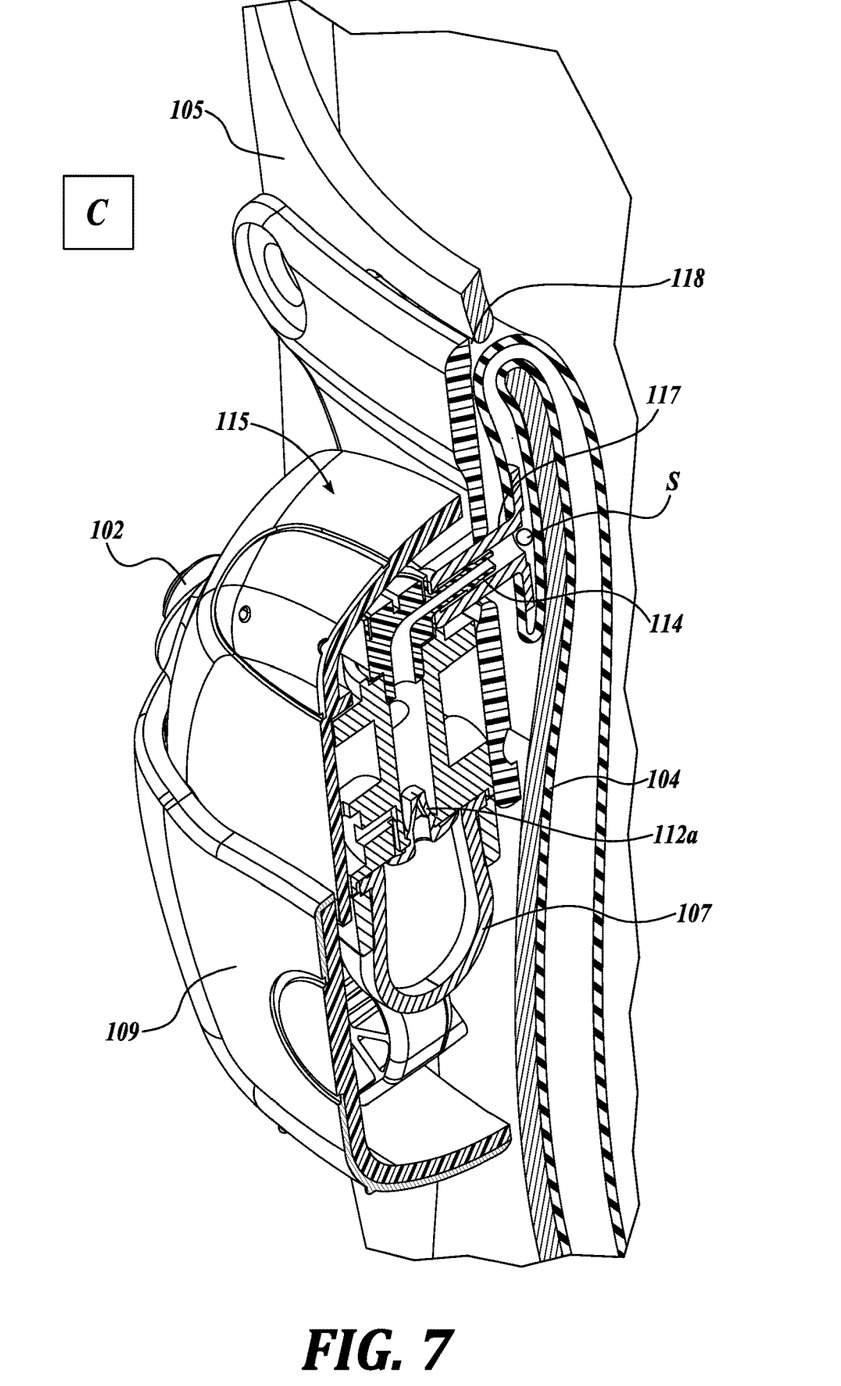
FIG. 7 is a cross-sectional perspective view of a prosthetic volume compensation system in accordance with an embodiment of the present technology.

FIG. 7 is a cross-sectional perspective view of a prosthetic volume compensation system in accordance with an embodiment of the present technology. By pressing the pump lever 109 up and down, the user pressurizes fluid inside a pressure bulb 107. The pressurized fluid may flow through a one-way valve 112*a*, and further through a connection between a barb (also referred to as a high-pressure outlet) 114 of the pump and the bladder port 117 to the bladder 104.

In some embodiments, a manual or motorized pump assembly 101 includes a sensor S (e.g., a pressure sensor, an accelerometer, a gyroscope, etc.) and a microcontroller C that is operationally coupled with one or more sensors S. The term "controller" as used herein encompasses devices capable of receiving data, processing data, and issuing command data. Such controllers include wearable computers, mobile telephones, tablets, and the like. The sensor S and the controller C may communicate wirelessly or through electrical wires.

In some embodiments, controller C may provide status indication of healthy standing pressures, thus providing a safety enhancement for the amputee population having neuropathy with limited sense of pain or pressure. For example, an amputee that suffers from neuropathy may operate a manual or a motorized pump until the controller indicates that a standing target pressure is reached.

Figure 7A:
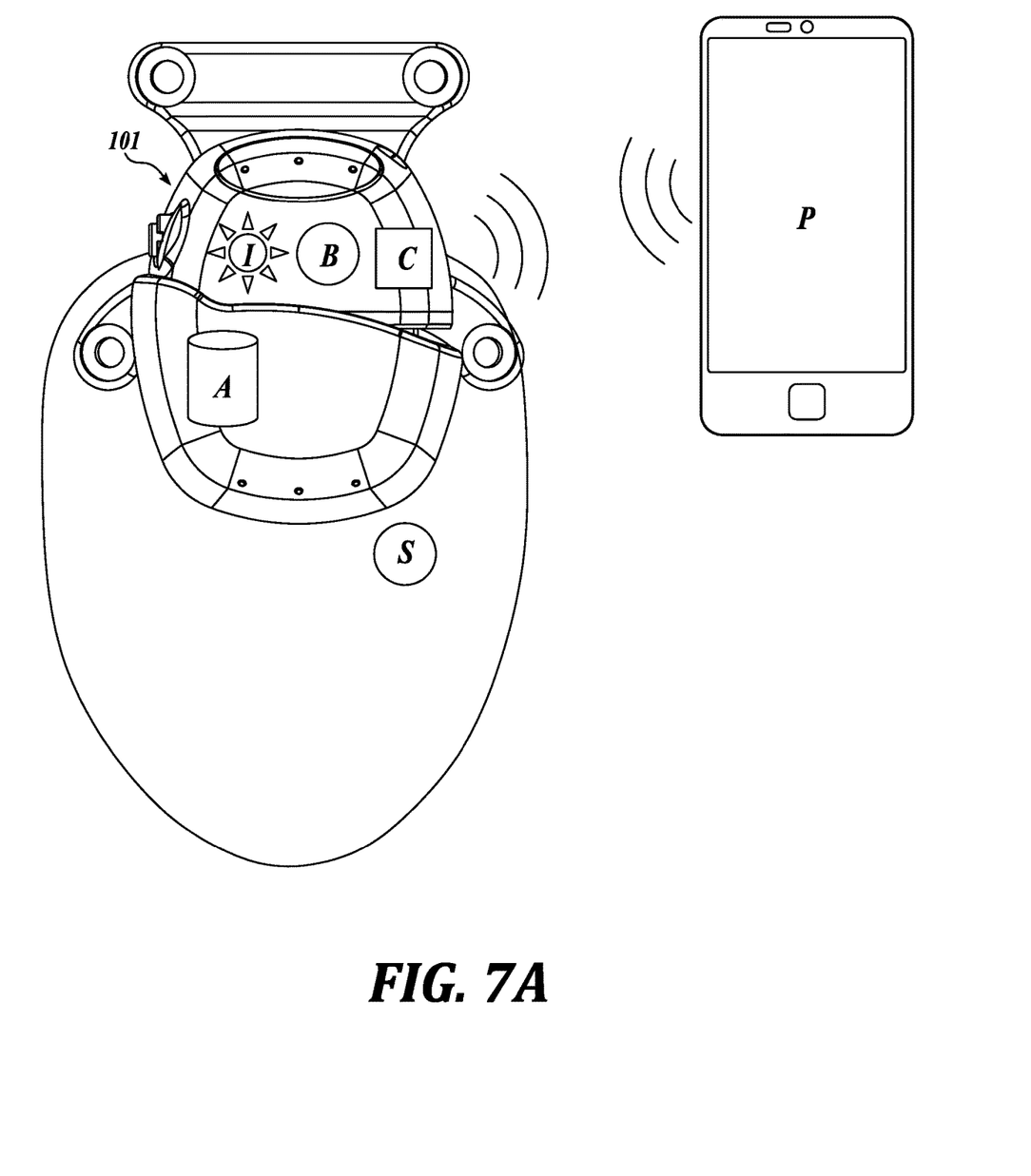
FIG. 7A is a schematic view of an automized prosthetic volume compensation system in accordance with an embodiment of the present technology.

FIG. 7A is a schematic view of an automized prosthetic volume compensation system in accordance with an embodiment of the present technology. In some embodiments, a manual or motorized pump assembly 101 includes a sensor S (e.g., a pressure sensor, accelerometers, gyroscopes, etc.) and a microcontroller C that is operationally coupled with one or more sensors S and powered by battery B. One or more actuators A may be included and operationally coupled to microcontroller C to drive a pump or control the bleed valve. The term "controller" as used herein encompasses devices capable of receiving data, processing data, and issuing command data. Such controllers include wearable computers, mobile telephones, tablets, and the like. The sensor(s) S and the controller C may communicate wirelessly or through electrical wires.

In some embodiments, controller C may provide status indication of current standing pressure, thus providing a safety enhancement for the amputee population having neuropathy with limited sense of pain or pressure. The status indication (e.g. pressure too high or pressure too low) may be communicated to a mobile phone P or by triggering indicator I, which could be a light or audible sound. In some embodiments, controller C may receive commands from mobile phone P to activate actuators A for the purpose of adjusting pressure. For example, an amputee that suffers from neuropathy may remotely operate a motorized pump or bleed valve until the controller indicates that a healthy standing target pressure is reached.

Figure 8:
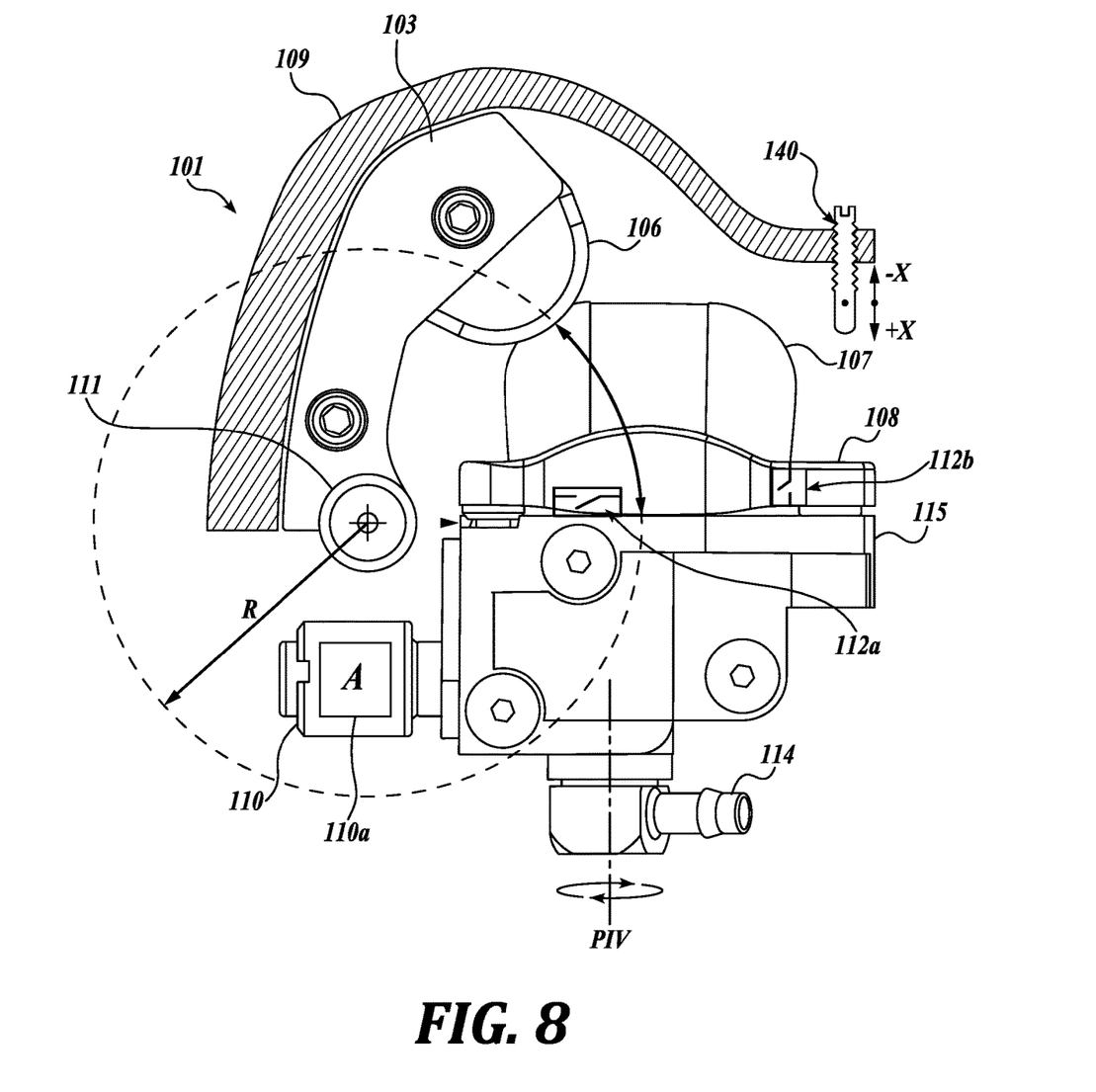
FIG. 8 is a partially schematic view of a prosthetic volume compensation system in accordance with an embodiment of the present technology.

FIG. 8 is a partially schematic view of a prosthetic volume compensation system in accordance with an embodiment of the present technology. In operation, an amputee pushes the pump lever 109, which in turn drives the pump actuator 103, causing a plunger 106 to press against a pressure bulb 107, which may be made from elastomer. In response, the pressure bulb 107 partially collapses, therefore increasing pressure inside the pressure bulb, thus causing the pressurized fluid to flow through a one-way valve 112*a* and a high-pressure outlet (also referred to as a barb for simplicity and brevity) 114 toward the bladder 104. In some embodiments, the high-pressure outlet 114 may be pivotable about axis PIV. As the pump actuator 103 is brought away from the pressure bulb 107, the pressure bulb recovers to its uncrumpled shape driven by elasticity of the pressure bulb. In some embodiments, air intake into the pressure bulb 107 is provided through a one-way valve 112*b*. In some embodiments, the one-way valves 112*a* and 112*b* may be combinable into a single valve.

In some embodiments, a bulb retainer 108 includes a preload arc and graduated profile. Therefore, as bulb retainer screws are tightened to close the initial gap, the bulb retainer 108 deforms to make intimate contact with the opposing planar surface of a pump frame 115. As a result, a relatively uniform compressive pressure is established across the interface between the flange of the pressure bulb 107, bulb retainer 108 and pump frame 115, thus improving the seal integrity of the pressure bulb 107.

The pump assembly 101 may include a bleed valve 110 that can be operated by the bleed actuator. In some embodiments, the bleed valve 110 may include a pressure relief valve 110*a* having a cracking pressure set to limit applied pressure to remain within safe values. The pressure relief valve 110*a* may be a pre-set, passive crack valve or may be actuated by an actuator A. In other embodiments, the pressure relief valve 110*a* may be separated from the bleed valve 110*a*. A pre-set pressure limit may be useful to amputees having lack of feeling in their limb (i.e., suffering from neuropathy).

The maximum achievable pressure within the pressure bulb 107 is determined in part by radius R of the pump actuator 103 and by the allowable travel of the pump actuator 103. For example, the maximum travel of the pump actuator 103 may be adjustable by a set screw 140 that determines a maximum crumpling of, and therefore a maximum pressure produced by the pressure bulb 107. In different embodiments, other travel limiters may be used to limit the travel of the pump actuator 103. In some embodiments, the position of the travel embodiment can be set by a qualified prosthetist.

Figure 9A:
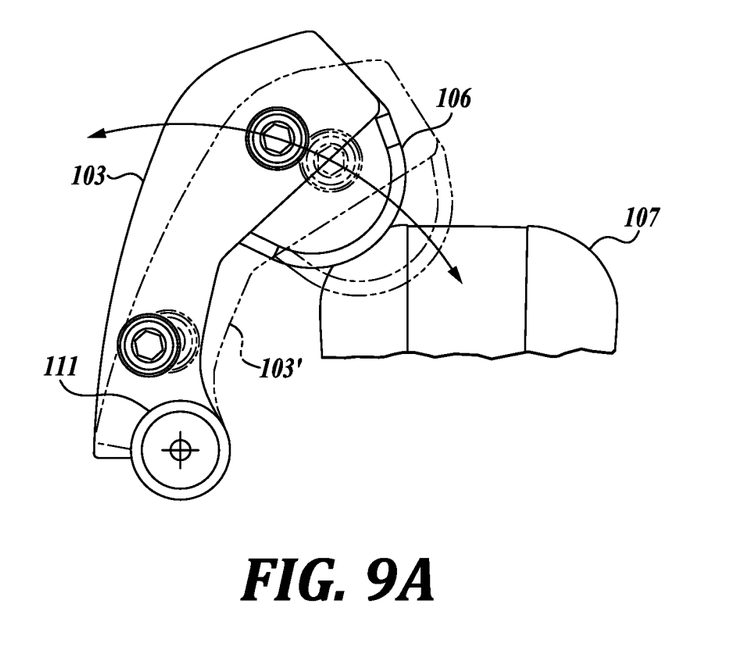
FIGS. 9A and 9B are partially schematic views of prosthetic volume compensation systems in accordance with an embodiment of the present technology.

FIG. 9A is a partially schematic view of prosthetic volume compensation systems in accordance with an embodiment of the present technology. The illustrated schematic shows the pump actuator 103 in two different positions. In the first position indicated by the solid lines, the plunger 106 moves into the pressure bulb 107, resulting in a certain volume displacement of the pressure bulb 107. In the second position 103' of the pump actuator, the pressure of the fluid inside the pressure bulb 107 is increased. In addition to increasing the travel of the pump actuator 103, the maximum pressure of the fluid inside the pressure bulb 107 can also be increased by having the pump actuator 103 press against a center point of the pressure bulb 107.

Figure 9B:
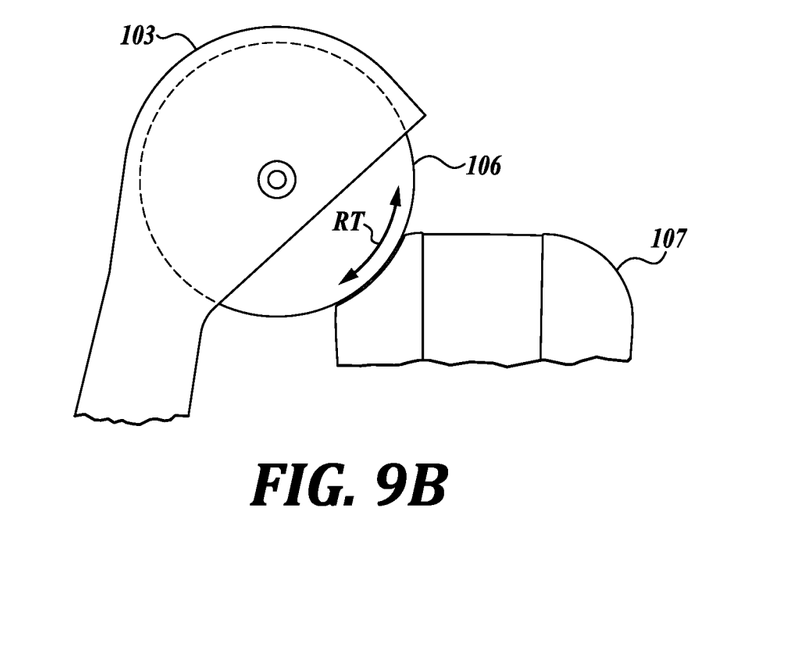

FIG. 9B is a partially schematic view of prosthetic volume compensation systems in accordance with an embodiment of the present technology. In the illustrated embodiment, the plunger 106 can rotate about its pivot point. In different embodiments, the plunger 106 may be a rubber wheel or a plastic wheel that rotates about its center point after making contact with the pressure bulb 107. Therefore, friction between the plunger 106 and the pressure bulb 107 is eliminated or at least reduced, resulting in increased lifetime of the pressure bulb 107.

Figure 10:
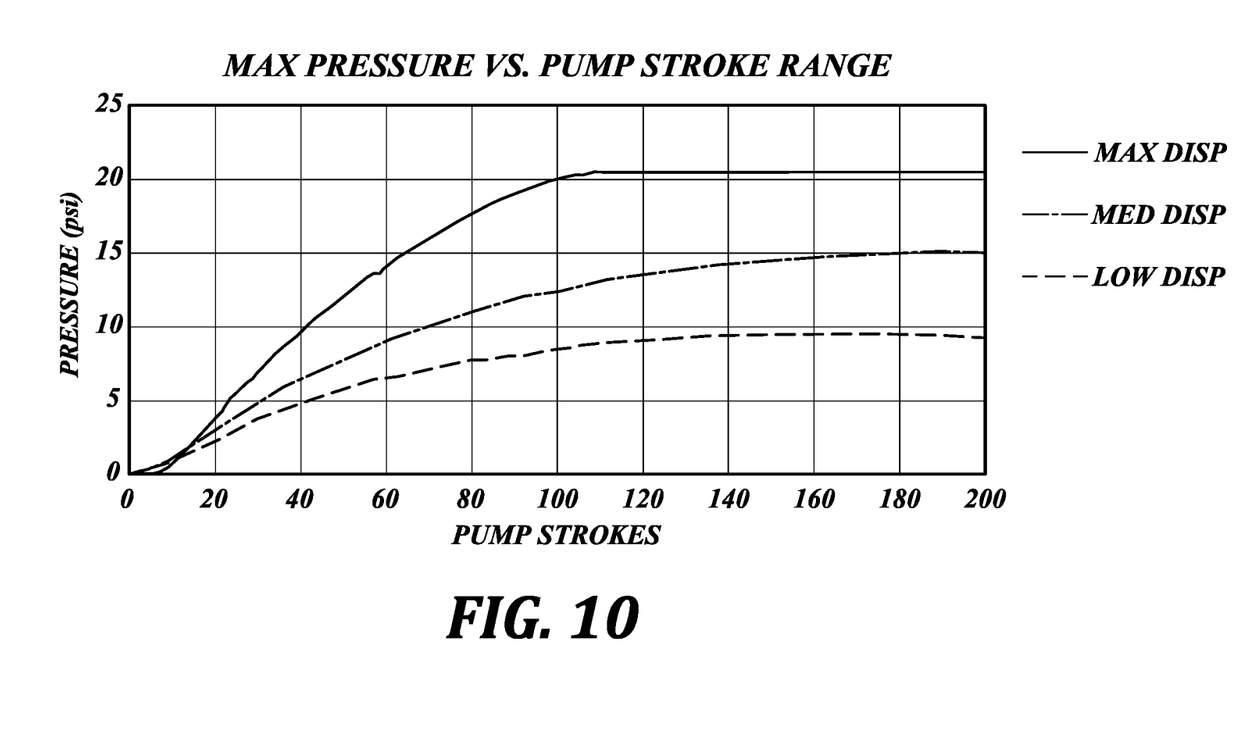
FIG. 10 is a graph of bladder pressures in accordance with an embodiment of the present technology.

FIG. 10 is a graph of bladder pressures in accordance with an embodiment of the present technology. The horizontal axis of the graph shows the number of pump strokes, i.e., the number of strokes of the pump actuator 103. The vertical axis of the graph shows pressure in the bladder 104. Multiple curves of the graph correspond to different displacements of the pressure bulb 107 that are adjustable by, for example, position of the set screw 140 or other travel limiter of the pump actuator 103. Three different travels/displacements are shown in the graph. In each case, the pressure curve asymptotes after a certain number of pump strokes, therefore providing an additional safety feature. For example, an amputee suffering from neuropathy is protected from exceeding a certain preset pressure in the prosthetics.

Figure 11:
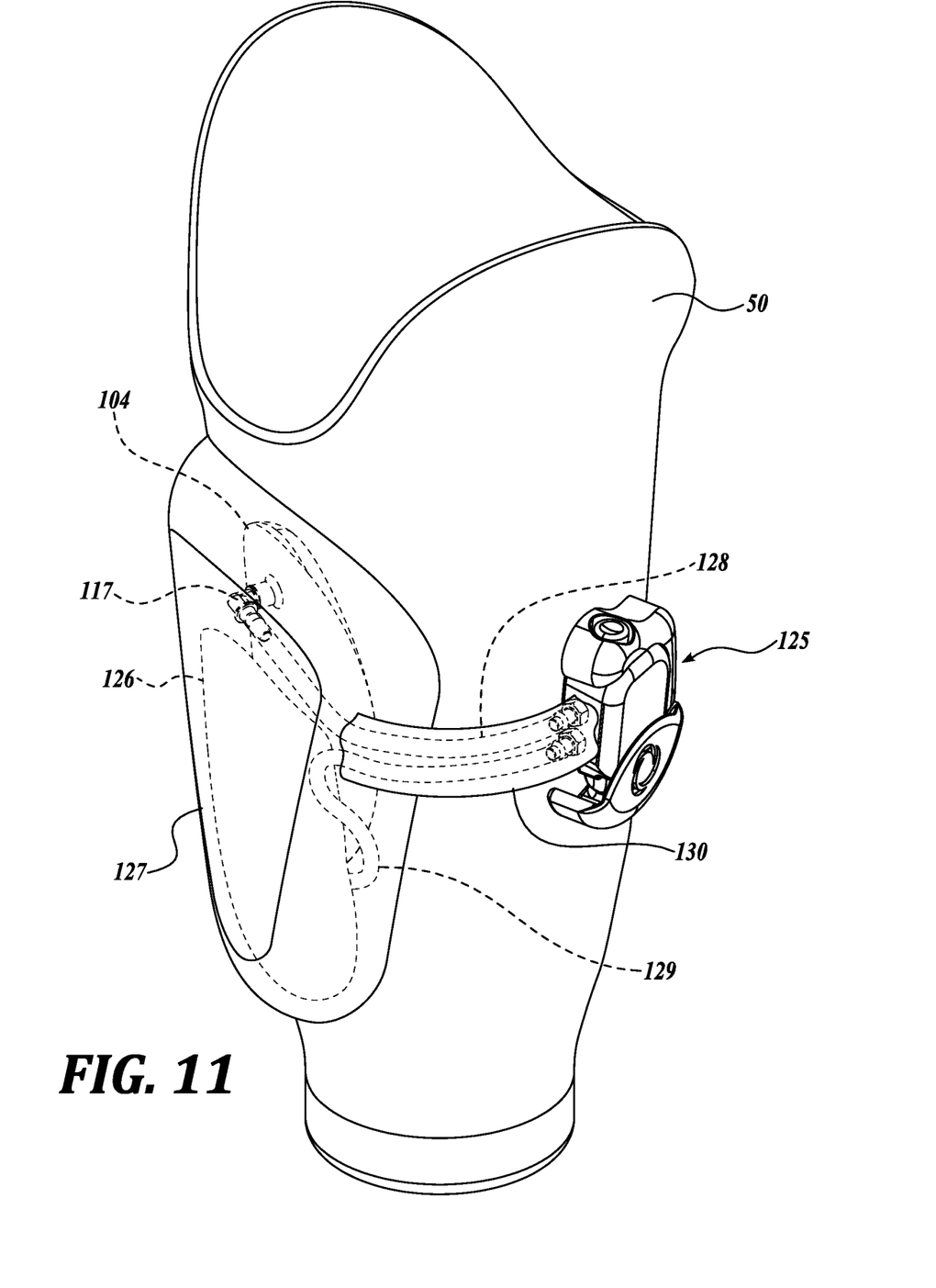
FIG. 11 is a perspective view of a hydraulic prosthetic volume compensation system in accordance with an embodiment of the present technology.

FIG. 11 is a perspective view of a hydraulic prosthetic volume compensation system in accordance with an embodiment of the present technology. The Illustrated system includes a liquid pump 125 that may achieve the target pressure/volume of the bladder with fewer pump strokes than a comparable gas pump, as the liquid medium is incompressible and the pump functions as a positive-displacement pump. In operation, high-pressure fluid is transferred from the liquid pump 125 through a high-pressure tubing 128. Conversely, low-pressure fluid is transferred to an external fluid reservoir 126. In some embodiments, the external fluid reservoir 126 is covered by a reservoir cover 127 as a protection from wear and damage. The bleed actuator may open a fluid passage between the high-pressure side and the low-pressure side when actuated, rather than venting the high-pressure into external environment as with the pneumatic (air) system.

In the illustrated embodiment, the liquid pump 125 is attached to the side of the prosthetic 50, and the external liquid reservoir 126 is attached to the back of the prosthetic 50. However, in different embodiments different locations may be selected for different parts of the system. In some embodiments, tubing cover 130 may contain and protect the high-pressure tubing 128 and low-pressure tubing 129 from wear and damage.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. A system for adjusting fit of a prosthetic device, the system comprising:
   a pump having a bleed actuator, a plunger and a pressure bulb; and
   a bladder fluidically coupled to the pump, wherein the bladder lines a posterior section of an interior of the prosthetic device, wherein a volume of the bladder is changeable by a pumping action of the pump, wherein the volume of the bladder at least partially determines a space available inside the prosthetic device, wherein the bleed actuator is configured to decrease the volume of the bladder, wherein the plunger in operation squeezes the pressure bulb of the pump, wherein a barb of the pump is directly connected to a bladder port of the bladder, and wherein the plunger comprises a rotating wheel that rotates when in contact with the pressure bulb.

2. The system of claim 1, further comprising the prosthetic device configured to receive a partial limb.

3. The system of claim 2, wherein a neck of the bladder protrudes through a slot on the prosthetic device.

4. The system of claim 1, wherein the pump is mounted to an outer posterior of the prosthetic device.

5. The system of claim 1, wherein the pump comprises a pump actuator configured to move along an up-down path.

6. The system of claim 5, wherein fluid is pumped into the bladder during upward strokes of the pump actuator.

7. The system of claim 5, wherein the bleed actuator is situated away from a top surface of the pump and away from the up-down path of the pump actuator such that the bleed actuator can be operated through clothing.

8. The system of claim 1, wherein the displacement of the plunger into the pressure bulb is adjustable, and wherein the displacement of the plunger at least in part determines a maximum pressure inside the bladder.

9. The system of claim 1, wherein the pressure bulb and the bladder are fluidically connected through a one-way valve and a pressure outlet.

10. The system of claim 1, further comprising:
    at least one sensor configured to measure the pressure inside the bladder;
    a controller configured to receive a sensor signal;
    a first actuator configured to drive the plunger; and
    a second actuator configured to open and close the bleed actuator in response to a controller signal.

11. The system of claim 1, wherein the pump is an air pump.

12. The system of claim 1, wherein the pump is liquid pump, wherein the bladder is fluidically coupled to the pump with a first pressure tubing, and wherein the bladder is fluidically coupled to an external liquid reservoir with a second pressure tubing.

13. A system for adjusting fit of a prosthetic device, the system comprising:
    a pump having a barb that is oriented toward a posterior of the prosthetic device, a bleed actuator, a plunger and a pressure bulb, wherein the plunger in operation squeezes the pressure bulb of the pump; and
    a bladder having a bladder port that is directly connected to the barb of the pump, wherein the bladder lines a posterior section of an interior of a prosthetic device, wherein a volume of the bladder is changeable by a pumping action of the pump, wherein the volume of the bladder at least partially determines a space available inside the prosthetic device, wherein the bleed actuator is configured to decrease the volume of the bladder, wherein a barb of the pump is directly connected to a bladder port of the bladder, and wherein the plunger comprises a rotating wheel that rotates when in contact with the pressure bulb.

\* \* \* \* \*